United States Patent
Lurie et al.

(12)
(10) Patent No.: US 6,224,562 B1
(45) Date of Patent: May 1, 2001

(54) METHODS AND DEVICES FOR PERFORMING CARDIOPULMONARY RESUSCITATION

(75) Inventors: Keith G. Lurie, Minneapolis; David G. Benditt, Edina, both of MN (US)

(73) Assignee: CPRX LLC, Minneapolis, MN (US)

( * ) Notice: Subject to any disclaimer, the term of this patent is extended or adjusted under 35 U.S.C. 154(b) by 0 days.

(21) Appl. No.: 09/197,286

(22) Filed: Nov. 20, 1998

Related U.S. Application Data

(63) Continuation of application No. 09/095,916, filed on Jun. 11, 1998.

(51) Int. Cl.$^7$ .................................................. A61H 31/00
(52) U.S. Cl. ................................................ 601/41; 607/42
(58) Field of Search .................................. 601/41; 600/9; 607/2, 3, 42, 152

(56) References Cited

U.S. PATENT DOCUMENTS

| | | | |
|---|---|---|---|
| 2,774,346 | 12/1956 | Halliburton | 128/29 |
| 3,191,596 | 6/1965 | Bird et al. | 128/29 |
| 3,662,751 | 5/1972 | Barkalow et al. | 128/145.8 |

(List continued on next page.)

FOREIGN PATENT DOCUMENTS

| | | |
|---|---|---|
| 668771 | 8/1963 | (CA) . |
| 2077608 | 3/1993 | (CA) . |
| 24 53 490 | 5/1975 | (DE) . |
| 0 029 352 | 5/1981 | (EP) . |
| 0 245 142 | 11/1987 | (EP) . |
| 0 411 714 A1 | 2/1991 | (EP) . |
| 0 509 773 A1 | 10/1992 | (EP) . |
| 1 465 127 | 11/1974 | (GB) . |
| 2 139 099 | 11/1984 | (GB) . |
| WO 90/05518 | 5/1990 | (WO) . |
| WO 94/26229 | 11/1994 | (WO) . |
| WO 95/13108 | 5/1995 | (WO) . |
| WO 096/28215 | 9/1996 | (WO) . |

OTHER PUBLICATIONS

Geddes, L.A., "Electrically Produced Artificial Ventilation," *Medical Instrumentation* 22(5): 263–271 (1988).

Glenn, William W.L., et al., "Twenty Years of Experience in Phrenic Nerve Stimulation to Pace the Diaphragm," *Pace* 9: 780–784 (Nov./Dec. 1986, Part I).

Kotze, P.L. et al., "Diaphragm Pacing in the Treatment of Ventilatory Failure," *Sant. Deel* 68:223–224 (Aug. 17, 1995).

Geddes, L.A. et al., "Inspiration Produced by Bilateral Electromagnetic, Cervical Phrenic Nerve Stimulation in Man," *IEEE Transactions on Biomedical Engineering* 38(9): 1047–1048 (Oct. 1991).

Geddes, L.A. et al., "Optimum Stimulus Frequency for Contracting the Inspiratory Muscles with chest Surface Electrodes to Produce Artificial respiration," *Annals of Biomedical Engineering* 18:103–108 (1990).

(List continued on next page.)

*Primary Examiner*—William E. Kamm
(74) *Attorney, Agent, or Firm*—Townsend and Townsend and Crew LLP

(57) ABSTRACT

Provided are exemplary devices and methods for increasing cardiopulmonary circulation when performing cardiopulmonary resuscitation. In one exemplary method, a patient's chest is actively compressed during a compression phase. At least some of the respiratory muscles are stimulated to contract during a decompression phase to cause an increase in the magnitude and duration of negative intrathoracic pressure during the decompression phase. In this way, the amount of venous blood flow into the heart and lungs is enhanced.

20 Claims, 8 Drawing Sheets

U.S. PATENT DOCUMENTS

| | | |
|---|---|---|
| 3,669,108 | 6/1972 | Sundblom et al. ............... 128/145.8 |
| 3,815,606 | 6/1974 | Mazal ............................... 128/351 |
| 3,834,383 | 9/1974 | Weigl et al. ..................... 128/145.8 |
| 4,041,943 | 8/1977 | Miller .............................. 128/145.8 |
| 4,077,404 | 3/1978 | Elam ............................... 128/145.8 |
| 4,166,458 | 9/1979 | Harrigan ........................... 128/24 |
| 4,226,233 | 10/1980 | Kritzer ............................. 128/205.13 |
| 4,259,951 | 4/1981 | Chernack et al. ................. 128/200.14 |
| 4,298,023 | 11/1981 | McGinnis .......................... 137/529 |
| 4,316,458 | 2/1982 | Hammerton-Fraser ........ 128/205.24 |
| 4,397,306 | 8/1983 | Weisfeldt et al. ................ 128/28 |
| 4,446,864 | 5/1984 | Watson et al. ................... 128/207.14 |
| 4,449,526 | 5/1984 | Elam ............................... 128/206.21 |
| 4,533,137 | 8/1985 | Sonne .............................. 272/99 |
| 4,601,465 | 7/1986 | Roy .................................. 272/99 |
| 4,809,683 | 3/1989 | Hanson ............................. 128/28 |
| 4,827,935 | 5/1989 | Geddes et al. ................... 128/419 |
| 4,881,527 | 11/1989 | Lerman ............................ 128/30.2 |
| 4,928,674 | 5/1990 | Halperin et al. ................. 128/30.2 |
| 5,014,698 | 5/1991 | Cohen ............................... 128/419 |
| 5,050,593 | 9/1991 | Poon ................................ 128/204.23 |
| 5,109,840 | 5/1992 | Daleiden ......................... 128/205.13 |
| 5,163,424 | 11/1992 | Kohnke ............................ 128/205.13 |
| 5,184,620 | 2/1993 | Cudahy et al. ................... 128/639 |
| 5,193,544 | 3/1993 | Jaffe ................................ 128/634 |
| 5,235,970 | 8/1993 | Augustine ........................ 128/200.26 |
| 5,301,667 | 4/1994 | McGrail et al. .................. 128/205.14 |
| 5,355,879 | 10/1994 | Brain ............................... 128/207.15 |
| 5,359,998 | 11/1994 | Lloyd .............................. 128/203.11 |
| 5,392,774 | 2/1995 | Sato ................................. 128/207.15 |
| 5,454,779 | 10/1995 | Lurie et al. ........................ 601/43 |
| 5,492,116 | 2/1996 | Scarberry et al. ............... 128/206.24 |
| 5,496,257 | 3/1996 | Kelly ................................ 601/41 |
| 5,517,986 | 5/1996 | Starr et al. ....................... 128/206.24 |
| 5,551,420 | 9/1996 | Lucie et al. ..................... 128/205.13 |
| 5,584,866 | 12/1996 | Kroll et al. ....................... 607/5 |
| 5,645,522 | 7/1997 | Lurie et al. ...................... 601/43 |
| 5,692,498 | 12/1997 | Lurie et al. ..................... 128/205.24 |
| 5,730,122 | 3/1998 | Lurie ............................... 128/207.12 |
| 5,735,876 | 4/1998 | Kroll et al. ....................... 607/5 |
| 5,738,637 | 4/1998 | Kelly et al. ...................... 601/41 |
| 5,782,883 | 7/1998 | Kroll et al. ....................... 607/14 |
| 5,814,086 | 9/1998 | Hirschberg et al. ............. 607/14 |

OTHER PUBLICATIONS

Laghi, Franco et al., "Comparison of Magnetic and Electrical Phrenic Nerve Stimulation in assessment of Diaphragmatic Contractility," *American Physiological society*, pp. 1731–1742 (1996).

Glenn, William W.L. et al., "Diaphragm Pacing by Electrical Stimulation of the Phrenic Nerve," *Neurosurgery* 17(6): 974–984 (1985).

Dupuis, Yvon G., "Ventilators Theory and Clinical Application," *Mosby Company* 1986.

Ambu International A/S, "Directions for use fo Ambu CardioPump".

Cohen, Todd J. et al., "Active Compression–Decompression Resuscitation: A novel method of Cardopulmonary Resuscitation," *Department of Medicine and the Cardiovascular Research Institute, UC San Francisco*, (1992).

Cohen, Todd J. et al., "Active Compression–Decompression: A new method of cardiopulmonary Resuscitation," *JAMA* 267(21): 2916–2923 (Jun. 3, 1992).

Lindner, Karl H. et al., "Effects of Active compression–Decompression Resuscitation on Myocardial and Cerebral Blood Flow in Pigs" *Department of Anesthesiology and Critical Care Medicine, University of Ulm, Germany* (Oct. 7, 1993).

Lurie, Keith G. et al., "Regulated to Death: The Matter of Informed Consent for Human Experimentation in Emergency Resuscitation Research," *Cardiac Arrhythmia Center at the University of Minnesota* 18:1443–1447 (Jul. 1995).

Fig. 7
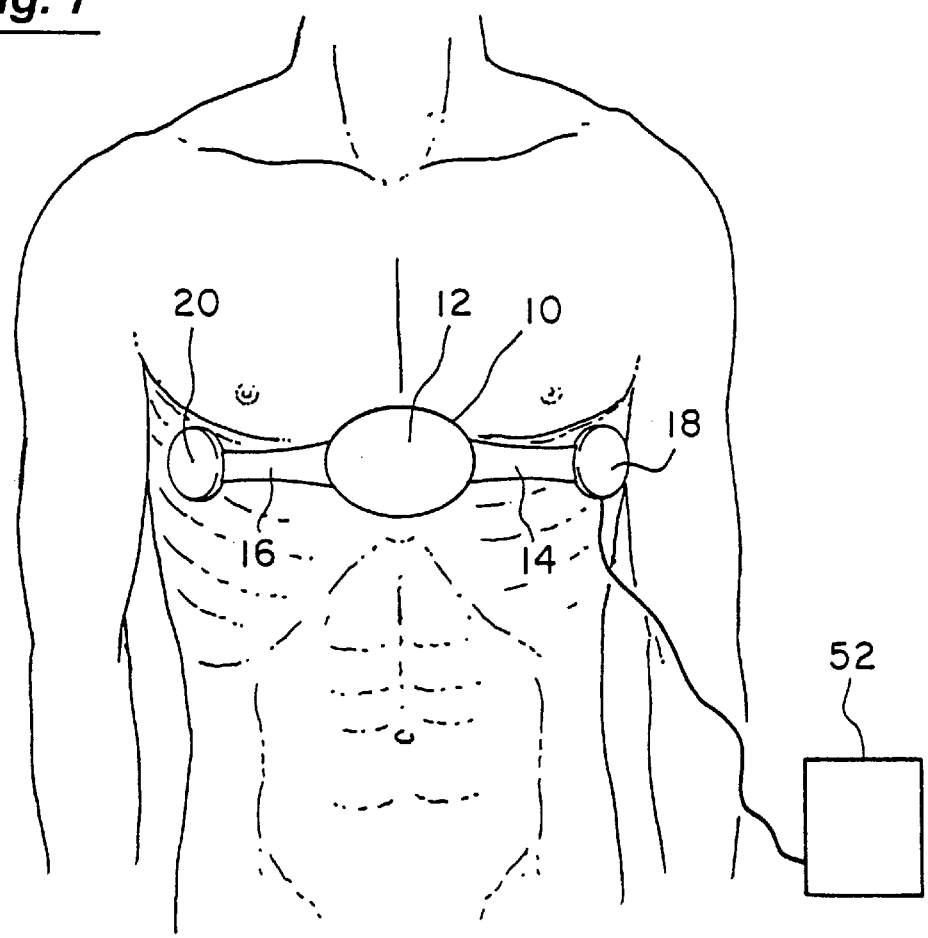
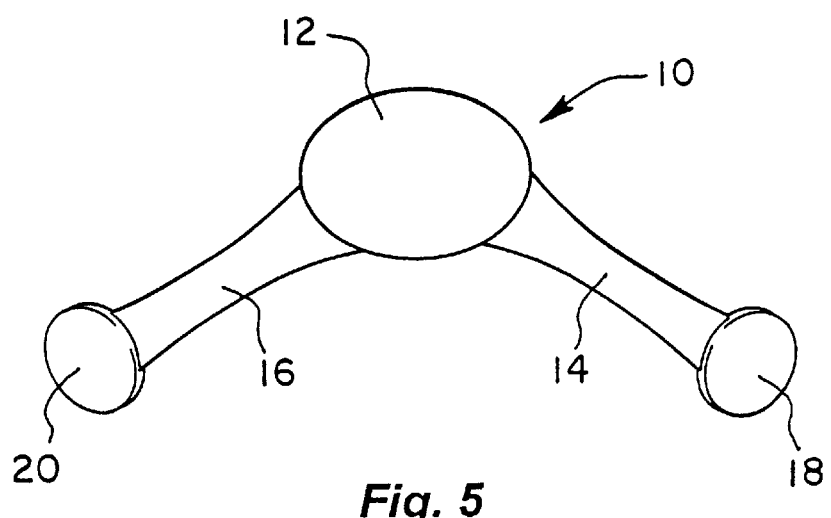
Fig. 5

METHODS AND DEVICES FOR PERFORMING CARDIOPULMONARY RESUSCITATION

CROSS REFERENCE TO RELATED APPLICATIONS

This application is a continuation in part application of U.S. patent application Ser. No. 09/095,916, filed Jun. 11, 1998, the complete disclosure of which is herein incorporated by reference.

BACKGROUND OF THE INVENTION

The invention relates generally to the field of cardiopulmonary resuscitation. In particular, the present invention relates to devices and methods for increasing cardiopulmonary circulation during cardiopulmonary resuscitation procedures involving a chest compression phase and a relaxation or decompression phase.

Worldwide, sudden cardiac arrest is a major cause of death and is the result of a variety of circumstances, including heart disease and significant trauma. In the event of a cardiac arrest, several measures have been deemed to be essential in order to improve a patient's chance of survival. These measures must be taken as soon as possible to at least partially restore the patient's respiration and blood circulation. One common technique, developed approximately 30 years ago, is an external chest compression technique generally referred to as cardiopulmonary resuscitation (CPR). CPR techniques have remained largely unchanged over the past two decades. With traditional CPR, pressure is applied to a patient's chest to increase intrathoracic pressure. An increase in intrathoracic pressure induces blood movement from the region of the heart and lungs towards the peripheral arteries. Such pressure partially restores the patient's circulation.

Traditional CPR is performed by active compressing the chest by direct application of an external pressure to the chest. This phase of CPR is typically referred to as the compression phase. After active compression, the chest is allowed to expand by its natural elasticity which causes expansion of the patient's chest wall. This phase is often referred to as the relaxation or decompression phase. Such expansion of the chest allows some blood to enter the cardiac chambers of the heart. The procedure as described, however, is insufficient to ventilate the patient. Consequently, conventional CPR also requires periodic ventilation of the patient. This is commonly accomplished by a mouth-to-mouth technique or by using positive pressure devices, such as a self-inflating bag which delivers air through a mask, an endotracheal tube, or other artificial airway.

In order to increase cardiopulmonary circulation induced by chest compression, a technique referred to as active compression-decompression (ACD) has been developed. According to ACD techniques, the active compression phase of traditional CPR is enhanced by pressing an applicator body against the patient's chest to compress the chest. Such an applicator body is able to distribute an applied force substantially evenly over a portion of the patient's chest. More importantly, however, the applicator body is sealed against the patient's chest so that it may be lifted to actively expand the patient's chest during the relaxation or decompression phase. The resultant negative intrathoracic pressure induces venous blood to flow into the heart and lungs from the peripheral venous vasculature of the patient. Devices and methods for performing ACD to the patient are described in U.S. Pat. Nos. 5,454,779 and 5,645,552, the complete disclosures of which are herein incorporated by reference.

Another successful technique for increasing cardiopulmonary circulation is by impeding air flow into a patient's lungs during the relaxation or decompression phase. By impeding the air flow during the relaxation or decompression phase, the magnitude and duration of negative intrathoracic pressure is increased. In this way, the amount of venous blood flow into the heart and lungs is increased. As a result, cardiopulmonary circulation is increased. Devices and methods for impeding or occluding the patient's airway during the relaxation or decompression phase are described in U.S. Pat. Nos. 5,551,420 and 5,692,498 and co-pending U.S. application Ser. No. 08/950,702, filed Oct. 15, 1997. The complete disclosures of all these references are herein incorporated by reference.

The above techniques have proven to be extremely useful in enhancing traditional CPR procedures. As such, it would be desirable to provide still further techniques to enhance venous blood flow into the heart and lungs of a patient from the peripheral venous vasculature during both conventional and alternative CPR techniques. It would be particularly desirable to provide techniques which would enhance oxygenation and increase the total blood return to the chest during the relaxation or decompression phase of CPR.

SUMMARY OF THE INVENTION

The invention provides methods and devices for increasing cardiopulmonary circulation when performing cardiopulmonary resuscitation. The methods and devices may be used in connection with most generally accepted CPR methods. In one exemplary method, a patient's chest is actively compressed during the compression phase of CPR. At least some of the respiratory muscles are then stimulated to contract during the relaxation phase to increase the magnitude and prolong the duration of negative intrathoracic pressure during the relaxation or decompression phase, i.e., respiratory muscle stimulation increases the duration and degree that the intrathoracic pressure is below or negative with respect to the pressure in the peripheral venous vasculature. By enhancing the amount of venous blood flow to the heart and lungs, cardiopulmonary circulation is increased.

Among the respiratory muscles that may be stimulated to contract are the diaphragm, the abdomen and the chest wall muscles, including the intercostal muscles. The respiratory muscles may be stimulated to contract in a variety of ways. For example, the diaphragm may be stimulated to contract by supplying electrical current or a magnetic field to various nerves or muscle bundles which when stimulated cause the diaphragm or abdominal muscles to contract. Similar techniques may be used to stimulate the chest wall muscles to contract. Alternatively, an upward thrust may be provided to the abdomen to cause the diaphragm to contract. A variety of pulse trains, pulse widths and pulse waveforms may be used for stimulation. In one preferred aspect, electrical current or a magnetic field is provided to the phrenic nerve.

To electrically stimulate the inspiratory motor nerves, electrodes are preferably placed on the lateral surface of the neck over the motor point for the phrenic nerve, on the chest surface just lateral to the lower sternum to deliver current to the phrenic nerves just as they enter the diaphragm, or on the upper chest just anterior to the axillae to stimulate the thoracic nerves. However, it will be appreciated that other electrode sites may be employed. For example, in one embodiment the respiratory muscles are stimulated by a transcutaneous electrical impulse delivered along the lower antero-lat margin of the rib cage.

A variety of other techniques may be applied to further enhance the amount of venous blood flow into the heart and lungs during the chest relaxation or decompression phase of CPR. For example, the chest may be actively lifted during the relaxation or decompression phase to increase the amount and extent of negative intrathoracic pressure. In another technique, air flow to the lungs may be periodically occluded during at least a portion of the relaxation or decompression phase. Such occlusion may be accomplished by placing an impedance valve into the patient's airway, with the impedance valve being set to open after experiencing a predetermined threshold negative intrathoracic pressure.

In one particular aspect of the method, respiratory gases are periodically supplied to the patient's lungs to ventilate the patient. In another aspect, a metronome is provided to assist the rescuer in performing regular chest compressions.

In still another aspect, the respiratory muscles are stimulated only during certain relaxation or decompression phases, such as every second or third relaxation or decompression phase. In yet another aspect, a defibrillation shock is periodically delivered to the patient to shock the heart or an electrical impulse is delivered to periodically initiate transthoracic pacing.

The invention further provides an exemplary device to assist in the performance of a cardiopulmonary resuscitation procedure. The device comprises a compression member which is preferably placed over the sternum and manually or mechanically pressed to compress the chest. At least one electrode is coupled to the compression member in a way such that the electrode will be positioned to supply electrical stimulation to the respiratory muscles to cause the respiratory muscles to contract following compression of the chest.

In one preferable aspect, a pair of arms extend from the compression member, with one or more electrodes being coupled to the end of each arm. Preferably, the arms are fashioned so as to be adapted to be received over the lower rib cage when the compression member is over the sternum. In this way, the electrodes are placed in a preferred location to stimulate the respiratory muscles to contract. Conveniently, the arms may be fashioned of a flexible fabric so that the arms will conform to the shape of the chest, thereby facilitating proper placement of the electrodes. In one preferable aspect, the electrodes comprise adhesive electrically active pads.

In one particular aspect, a voltage controller or a potentiometer is provided to control the voltage at the electrode. In this way, the rescuer may change the voltage output of the electrode to ensure adequate respiratory muscle stimulation. A metronome may optionally be provided and incorporated into the device to assist a rescuer in performing regular chest compressions with the compression member.

In one particularly preferable aspect, a pressure or force sensor is disposed in the compression member to sense when a compressive force is being applied to the compression member. An actuator is preferably also provided to cause actuation of the electrode when the sensor senses an external compression that is being applied to the compressive member. In this way, a sensor-directed electrical impulse may be emitted from the electrode to transcutaneously stimulate the respiratory muscles to contract at the end of the compression phase. In cases where a significant delay occurs between delivery of the stimulant and full respiratory muscle contraction, the sensor may be employed to sense when mid-compression (or some other point in the compression phase) occurs to initiate respiratory muscle stimulation sometime before the start of the relaxation or decompression phase.

In still another aspect, a power source is coupled to the electrode. The power source may be integrally formed within the device or may be a separate power source which is coupled to the electrode. As another alternative, the electrode may be coupled to a defibrillator to provide a defibrillation shock or to initiate trans-thoracic pacing. In another aspect, the voltage controller and power source may be part of a sensor-compression-stimulation device or coupled to the device but separated from the compression-sensor-stimulation device. In still another alternative, the device may be coupled to a ventilator to periodically ventilate the patient based on the number of compressions. In another aspect, impedance or electrical impulses generated by chest compression may be sensed and used by a remote power source and pacer-defibrillation unit to stimulate decompression phase respiratory muscle stimulation using the same sensing electrode(s) or other means to also stimulate the respiratory muscles to contract.

The invention further provides an exemplary device to assist in the performance of cardiopulmonary resuscitation by stimulating the phrenic nerve to cause the diaphragm or other respiratory muscles to contract during the relaxation or decompression phase of CPR. Such stimulation may be accomplished by delivering either electrical or magnetic energy to the phrenic nerve. In one embodiment, the phrenic nerve stimulators may be coupled to a chest compression sensor to coordinate chest compressions with the supply electric current or magnetic stimulation to the phrenic nerve.

In another embodiment, the device comprises a ventilation member which is coupled to the patient's airway to assist in the flow of respiratory gases into the patient's lungs. An electrode is coupled to the ventilation member to supply an electrical current to the phrenic nerve to cause the diaphragm or other respiratory muscles to contract. In this way, a ventilation member which is typically employed to provide ventilation to a patient during a CPR procedure may also function as a stimulant to cause contraction of the diaphragm or other respiratory muscles during the relaxation or decompression phase of CPR. In this manner, the amount of venous blood flowing to the heart and lungs will be enhanced.

A variety of ventilation members may be employed, including endotracheal tubes, laryngeal mask airways, or other ventilation devices which are placed within the larynx, esophagus, or trachea. In one particularly preferable aspect, a pair of electrodes is coupled to the ventilation member so that the device may operate in a bipolar manner to stimulate the phrenic nerve. Other aspects include transcutaneous phrenic nerve stimulation with a collar-like device placed around the neck which includes one or more electrodes to stimulate the phrenic nerve.

BRIEF DESCRIPTION OF THE DRAWINGS

FIG. 5 is a top plan view of an alternative embodiment of a respiratory muscle stimulation device according to the invention.

FIG. 7 illustrates the device of FIG. 1 when used to treat a patient according to the invention.

DETAILED DESCRIPTION OF THE SPECIFIC EMBODIMENTS

Figure 1:
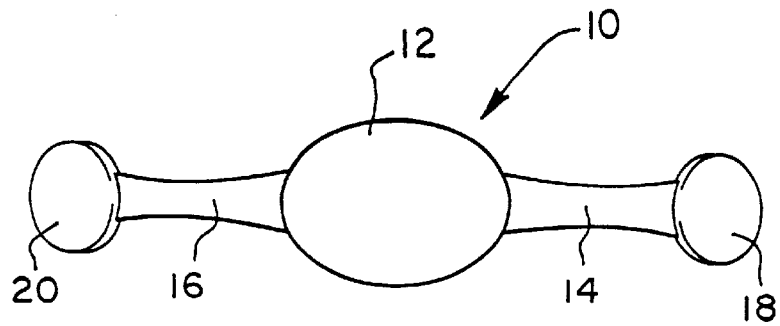
FIG. 1 is a top plan view of an exemplary respiratory muscle stimulation device according to the invention.

The present invention provides methods and devices for increasing cardiopulmonary circulation when performing cardiopulmonary resuscitation. As is known in the art, cardiopulmonary resuscitation techniques involve a compression phase where the chest is compressed and a relaxation phase where the chest is allowed to return to its normal position. The methods and devices of the invention may be used in connection with any method of CPR in which intrathoracic pressures are intentionally manipulated to improve cardiopulmonary circulation. For instance, the present invention may be used in connection with standard, manual, closed-chest CPR, interposed abdominal counterpulsation CPR, with a mechanical resuscitator, such as the Michigan Instruments "Thumper", with ACD-CPR, with "Lifestick" CPR, and the like.

In a broad sense, the present invention provides for stimulating contraction of at least some of the respiratory muscles during the relaxation or decompression phase of CPR to enhance and sustain the duration of negative intrathoracic pressure during the relaxation or decompression phase. The significance of the increase in negative intrathoracic pressure during the relaxation or decompression phase is that more venous blood is forced into the chest from the peripheral venous vasculature. As a result, more blood is allowed to be oxygenated and more blood is forced out of the chest during the next compression. Upon contraction of the respiratory muscles, the patient will typically "gasp". The invention thus provides techniques for consistently inducing a "gasp" after chest compression.

The respiratory muscles that may be stimulated to contract include the diaphragm, the abdominal muscles and the chest wall muscles, including the intercostal muscles. Specific chest wall muscles that may be stimulated to contract include those that elevate the upper ribs, including the scaleni and sternocleidomastoid muscles, those that act to fix the shoulder girdle, including the trapezii, rhomboidei, and levatores angulorum scapulorum muscles, and those that act to elevate the ribs, including the serrati antici majores, and the pectorales majores and minores as described generally in Leslie A. Geddes, "Electroventilation—A Missed Opportunity?", *Biomedical Instrumentation & Technology*, July/August 1998, pp. 401–414, the complete disclosure of which is herein incorporated by reference. Of the respiratory muscles, the two hemidiaphragms appear to be the greatest contributors to inspiration and expiration.

The invention provides a variety of ways to stimulate respiratory muscle contraction so that the magnitude and extent of negative intrathoracic pressure during the relaxation or decompression phase may be increased. Preferably, the respiratory muscles are stimulated to contract by transcutaneous electrical field stimulation techniques. For example, to stimulate the diaphragm, the phrenic nerve may be stimulated in the neck region near C3, C4 or C5, or where the phrenic nerves enter the diaphragm. Alternative techniques for stimulating diaphragmatic contraction include an abdominal thrust or by magnetic field stimulation of the diaphragm or the phrenic nerve. Magnetic field stimulation may also be employed to stimulate the chest wall muscles. Electrical field stimulation of the diaphragm or the chest wall muscles is preferably accomplished by placing one or more electrodes on the skin, preferably in the vicinity of the neck or the lower rib cage (although other locations may be employed) and then providing electrical current to the electrode to stimulate the respiratory muscles to contract. Still further, subcutaneous electrodes may also be used to stimulate respiratory muscle contraction.

The respiratory muscle stimulation techniques of the invention may be used in connection with or in close association with various other techniques designed to treat or diagnose the patient receiving CPR. For example, during the relaxation or decompression phase, the patient's airway may be occluded to prevent foreign (outside) air or respiratory gases from flowing to the patient's lungs. In this way, the magnitude and duration of negative intrathoracic pressure during the relaxation or decompression phase are further enhanced. Exemplary devices and methods for occluding the patient's airway during the relaxation or decompression phase are described in U.S. Pat. Nos. 5,551,420 and 5,692,498 and co-pending U.S. application Ser. No. 08/950,702, previously incorporated herein by reference. As another example, the respiratory muscle stimulation techniques of the invention may be used in connection with ACD-CPR where the patient's chest is actively lifted during the relaxation or decompression phase to further enhance and sustain the duration of negative intrathoracic pressure during the relaxation or decompression phase.

The electrodes employed by the invention to stimulate respiratory muscle contraction may optionally be coupled to a defibrillator to deliver a defibrillation shock to the heart, or to supply energy to initiate transthoracic pacing. Since the device is preferably in contact with the skin, the device may optionally include various sensors to monitor various physiological parameters. For example, the device may include oxygen sensors, temperature sensors, or sensors to monitor $O_2$ saturation. Further, sensors may be provided to sense surface electrograms. The device may also be employed to deliver drugs transcutaneously.

In a preferred embodiment, an adhesive compressive pad is placed over the lower portion of the sternum. Compressions are applied as with standard manual CPR to a depth of about two to three inches. A sensor is incorporated in a compression region of the pad and is employed to signal the triggering of respiratory muscle contraction. Preferably, portions of the compressive pad are electrically active to stimulate diaphragmatic and/or chest wall muscle contraction upon receipt of a signal from the sensor.

Figure 2:
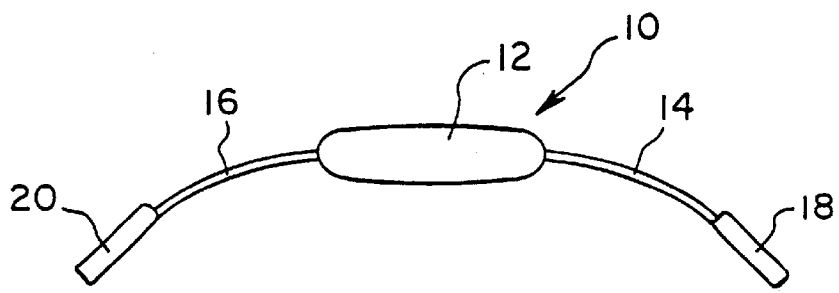
FIG. 2 is a side view of the device of FIG. 1.
Figure 3:
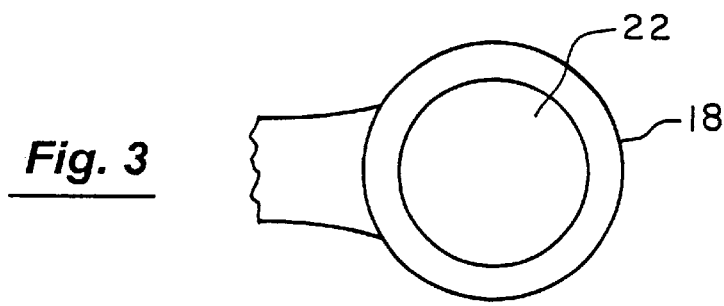
FIG. 3 is a detailed bottom view of an end member of the device of FIG. 1 showing an electrode for stimulating the respiratory muscles.

Referring now to FIGS. 1 and 2, an exemplary embodiment of a device 10 to provide respiratory muscle contraction during the performance of CPR will be described. Device 10 comprises a compression member 12 which is configured so that it may be received over the patient's chest in the area of the sternum. In this way, compression member 12 may be pressed downward to compress the patient's chest during the compression phase of CPR. Coupled to compression member 12 by a pair of arms 14 and 16 are a pair of end elements 18 and 20, respectively. As best shown in FIG. 3, end element 18 includes an electrode 22 on a bottom surface, it being appreciated that end element 20 or compression member 12 may include a similar electrode. Electrode 22 may comprise an adhesive electrically active pad, such as an R2 pad, commercially available from 3M. Electrodes 22 may also include a conductive gel. Other electrodes that may be employed include electrodes constructed of stainless steel, carbon-filled silicone rubber, platinum, iridium, silver silver-chloride, and the like. The electrode may be applied to the skin surface or may pierce the skin surface. It will also be appreciated that electrode 22 may be configured to operate in a monopolar manner, a bipolar manner or a multipolar manner. Further, electrode 22 may be configured to deliver electrical stimulation at different frequencies, pulse widths, pulse trains and voltage outputs to optimize respiratory muscle stimulation. The configuration of arms 14 may be varied to vary the lead vector produced by electrode 22. For example, the lead vector may be from one side of the chest to the other, to the mid-compression region, or from one lead to the other on the same side of the chest. Device 10 may also be configured to deliver an output based, at least in part, upon the chest wall impedance. An energy source is coupled to the electrodes to deliver low energies, e.g., about 0.01 amps to about 2 amps, and more preferably about 0.1 amps to about 1.0 amps, to stimulate the respiratory muscles.

Although electrodes 22 have been described as electrodes which provide electrical stimulation, it will be appreciated that device 10 can be modified to provide a magnetic field to stimulate the respiratory muscles to contract. For example, a magnetic field may be applied to the phrenic nerve to produce diaphragmatic and/or chest wall muscle stimulation. As such, an upper back pad may be needed for optimal phrenic nerve stimulation.

Exemplary techniques for stimulating the respiratory muscles, and particularly the diaphragm, to contract, including techniques for providing both electrical and magnetic stimulation of the inspiratory motor nerves, are described in L. A. Geddes, "Electrically Produced Artificial Ventilation," *Medical Instrumentation* 22(5): 263–271 (1988); William W. L. Glenn et al., "Twenty Years of Experience in Phrenic Nerve Stimulation to Pace the Diaphragm," *Pace* 9:780–84 (November/December 1986, Part 1); P. L. Kotze et al., "Diaphragm Pacing in the Treatment of Ventilatory Failure," *Sant. Deel* 68:223–224 Aug. 17, 1995); L. A. Geddes et al., "Inspiration Produced by Bilateral Electromagnetic, Cervical Phrenic Nerve Stimulation in Man," IEEE Transactions on *Biomedical Engineering* 38(9) :1047–1048 (October 1991); L. A. Geddes et al., "Optimum Stimulus Frequency for Contracting the Inspiratory Muscles with Chest-Surface Electrodes to Produce Artificial Respiration," *Annals of Biomedical Engineering* 18:103–108 (1990); Franco Laghi et al., "Comparison of Magnetic and Electrical Phrenic Nerve Stimulation in Assessment of Diaphragmatic Contractility," *American Physiological Society*, pp. 1731–1742 (1996); and William W. L. Glenn et al., "Diaphragm Pacing by Electrical Stimulation of the Phrenic Nerve," *Neurosurgery* 17(6):974–984 (1985). The complete disclosures of all these references are herein incorporated by reference in their entirety. The electrodes of the invention may be configured to operate in a monopolar manner, a bipolar manner, or a multi-polar manner.

Arms 14 and 16 are preferably constructed of a flexible material, including fabrics, such as a nylon fabric, elastomeric materials, including rubbers, plastics and the like, to facilitate proper placement of electrodes 20 on the patient optionally, arms 14 and 16 may be pivotally attached to compression member 12 to allow electrodes 20 to be placed at a variety of locations on the patient.

Figure 4:
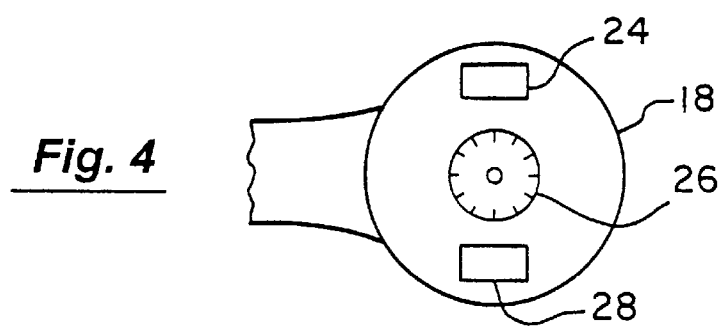
FIG. 4 illustrates a top view of the end member of FIG. 3 showing a potentiometer, a metronome, and a power source.

As illustrated in FIG. 4, a top side of end element 18 includes a metronome 24. Metronome 24 assists the rescuer in performing regular chest compressions when performing CPR by emitting regular audible or visual signals. This, in turn, aids in the coordinated timing between the compression of the chest and the stimulation of the respiratory muscles during the relaxation or decompression phase. End element 18 further includes a voltage controlling mechanism, such as a potentiometer 26, which enables the rescuer to change the voltage output of electrode 22 (see FIG. 3) to ensure adequate diaphragmatic stimulation. In one alternative, proper voltage may be determined automatically depending upon chest wall impedance that is measured with a impedance meter. In this way, device 10 may be configured so that it does not over stimulate or under stimulate the inspiratory motor nerves. End element 18 still further includes an energy source 28 which provides energy to the various electrical components, sensors, impedance meters, electrodes, and the like of device 10. Energy source 28 may conveniently comprise a battery that is stored within end element 18. Alternatively, a wide variety of external energy sources may be employed to operate device 10. For example, electrical energy may be provided by a ventilator which is employed to ventilate the patient, a defibrillator which may optionally be employed to provide defibrillation and transthoracic pacing and house the electrical components of a sensing system, an electrical generator which converts mechanical energy provided by the rescuer during compression of compression member 12 to electrical energy, and the like.

Although not shown, device 10 may optionally include a variety of displays, instructions for use, and controls that may be located on compression member 12, arms 14 or end elements 18. For example, device 10 may include a force, pressure or depth display which displays the amount of force, pressure or depth being applied to compression member 12 by the rescuer. In this way, the rescuer may be provided with information regarding the amount of force being supplied to compression member 12. Preferred force ranges may be included on device 10 so that the rescuer may determine if he is within a recommended force range. Device 10 may also include a compression counter display which displays the number of compressions experienced by compression member 12. The compression counter may be configured to display cycles of compressions to allow the rescuer to visualize the number of compressions that are performed for every respiratory muscle stimulation. Device 10 may still further include a surface electrogram sensing display to display information relating to a surface electrogram. Still further, a physiological parameter display may be provided to display various physiological parameters such as $O_2$ saturation, $CO_2$ saturation, skin temperature, and the like.

As shown in FIG. 5, device 10 may be provided with a wishbone configuration so that end elements 18 are placed over the lower margin of the rib cage. Arms 14 and 16 may be configured to be fixedly mounted relative to compression member 12 so that the electrodes will always be placed at about the same region on the chest. Alternatively, arms 14 and 16 may be movably mounted to compression member 12 so that the position of the electrodes on the patient may be adjusted. As previously described, arms 14 and 16 may be configured to be constructed of either a flexible or a rigid material to facilitate proper placement of the electrodes on the patient.

Figure 5A:
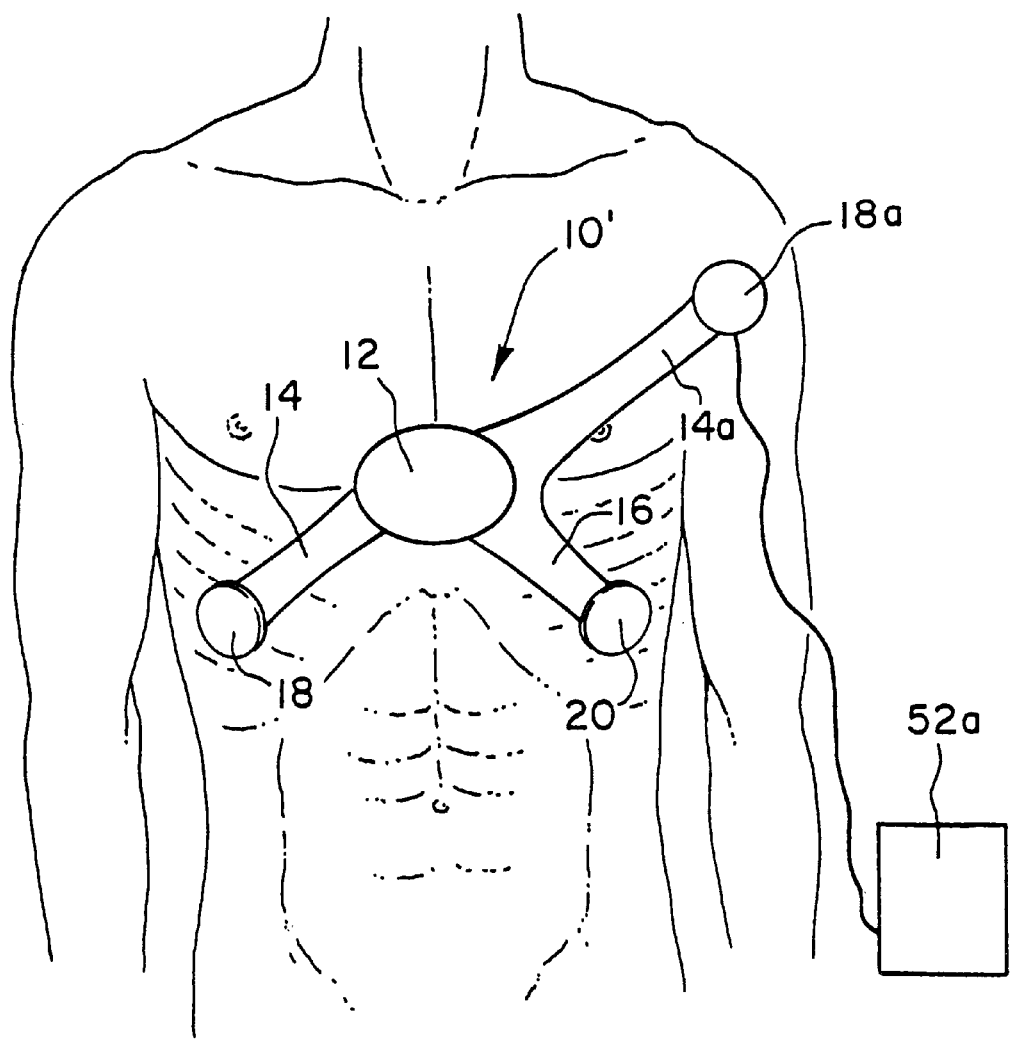
FIG. 5A illustrates yet another alternative embodiment of a respiratory muscle stimulation device according to the invention.

In another embodiment illustrated in FIG. 5A, a device 10' is provided which is similar to device 10 of FIG. 5 (with similar elements being labelled with the same reference numerals) and further includes an arm 14a having an end element 18a which is placed over the left axilla and has an electrode for defibrillation between the arm and the chest. In this way, compression member 12 may be placed over the sternum, with end elements 18 and 20 being placed over the lower rib cage to stimulate the respiratory muscles to contract between chest compressions as previously described. When needed, defibrillation may be provided by actuating the electrode on end element 18a. Optionally, a defibrillation unit 52a may be coupled to device 10'. Unit 52a includes an energy source for both diaphragmatic pacing and defibrillation. In this way, the energy source and other electrical components may be included within device 10' or in unit 52a.

Figure 6:
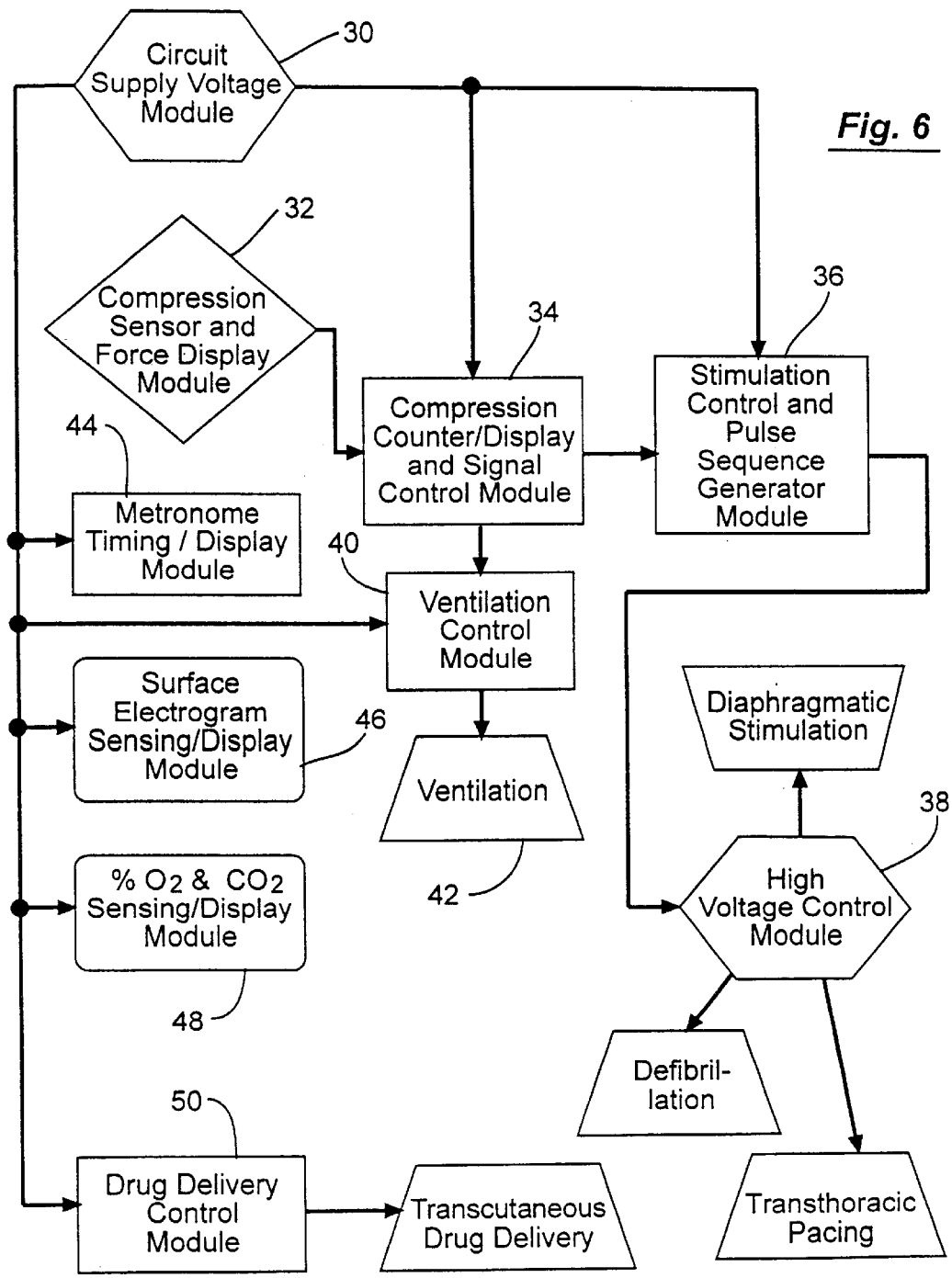
FIG. 6 is a schematic diagram of the circuitry of the device of FIG. 1 according to the invention.

Referring now to FIG. 6, a schematic diagram of the electrical components employed with device 10 will be described. Electrical power is provided to the various components with a circuit supply voltage module 30. Module 30 corresponds to energy source 28 of FIG. 4 and may comprise an internal or external power supply as previously described. A compression sensor and force display module 32 is provided to sense compression of compression member 12 (see FIG. 1) and to optionally display the force, pressure, and/or depth information to the rescuer. Exemplary compression sensors that may be employed include piezoelectric crystals that produce an electrical charge in proportion to the amount of force applied, fluid reservoirs and associated pressure sensors to detect an increase in pressure upon application of a force, strain gauges, and the like. Conveniently, the force detected by the compression sensor may be displayed on an LCD, LED or other display on device 10.

A compression counter/display and signal control module 34 is coupled to compression sensor 32 and counts each compression of compression member 12. The number of compressions may conveniently be displayed on device 10. Signals from module 34 are also transferred to a stimulation control and pulse sequence generator module 36 which is responsible for producing electrical signals employed by electrodes 22 (see FIG. 3). Module 36 is configured to produce an electrical pulse immediately after receipt of a counting logic signal from module 34. In this way, the electrodes may be actuated immediately after the compressive force is applied by the rescuer so that respiratory muscle stimulation is triggered to occur at the beginning of the relaxation or decompression phase of CPR. Module 36 preferably includes a signal generator to produce pulsed sequences resulting in the delivery of energy through the electrodes. Module 36 may be configured to produce pulses which correlate to every signal received from module 34 or only for selected signals from module 34. In this way, respiratory muscle stimulation may occur immediately after every compression or only after certain compressions.

In electrical communication with module 36 is a high voltage module 38 which functions to provide high voltage waveforms so that the electrodes may operate at the proper stimulation voltage level. Module 38 may be employed to operate the electrodes to provide respiratory muscle stimulation as shown. The applied voltage may be modified by the rescuer by operating potentiometer 26 (see FIG. 4). Additionally, module 38 may be employed to operate the electrodes so that they perform a defibrillation function or to accomplish transthoracic pacing as is known in the art. In this way, device 10 may be used to stimulate the respiratory muscles to contract during CPR as well as for defibrillation or transthoracic pacing.

Also in electrical communication with module 34 is a ventilation control module 40. Module 40 is optional and may be provided to receive electrical signals from module 34 indicating actuation of compression sensor 32. Module 40 is coupled to a ventilation device 42 which may be configured to periodically ventilate the patient in an automated manner based on actuation of compression sensor 32 as CPR is being performed. Preferably, module 40 will be configured to actuate the ventilator at a frequency of about one ventilation to every five compressions. As one example, control module 40 may be constructed similar to the module described in U.S. Pat. No. 4,397,306 to coordinate the actuation of ventilation device 42 with actuation of compression sensor 32. The complete disclosure of this reference is herein incorporated by reference. Although device 10 has been described as being coupled to an automated ventilation device, it will be appreciated that manual ventilation devices and a techniques may also be employed to ventilate the patient during the performance of CPR, whether or not electrically coupled to device 10. One advantage of providing ventilation control module 40 is that ventilation device 42 and high voltage control module 38 are electrically coupled so that coordination of ventilation, diaphragmatic pacing, cardiac pacing, and/or defibrillation may occur.

Device 10 may be modified so that the electrical components (such as those set forth in FIG. 6) and power source are provided in a separate unit. For example, such components may be incorporated into a defibrillator which in turn is coupled to device. In this way, device 10 may be manufactured relatively inexpensively, with the electrical components being provided in a separate unit. Further both diaphragmatic stimulation and pacing may be provided with a base unit which is coupled to device 10.

In one particular alternative, patient ventilation may be assisted with the use of a ventilation device having a threshold negative intrathoracic pressure device which opens when a predetermined negative intrathoracic pressure is reached during the relaxation or decompression phase as described in U.S. Pat. Nos. 5,692,498 and 5,551,420, previously incorporated by reference. With such a configuration, device 10 may be provided with a controller which is coupled to the threshold valve so that actuation of the threshold valve may be coordinated with diaphragmatic stimulation to optimize the negative intrathoracic pressure. In particular, the impedance threshold valve may be opened and closed using a servo- or electromagnetically-controlled circuit that is coupled to device 10 so that its operation may be coordinated with operation of the electrodes.

Still referring to FIG. 6, a metronome timing display module 44 is electrically coupled to circuit supply high voltage module 30 and is employed to produce regular audible and/or visual signals to assist the rescuer in performing regular chest compressions. A surface electrogram sensing/display module 46 is also electrically coupled to module 30 and allows for the sensing of surface electrograms and displaying the sensed information. Exemplary sensors for sensing surface electrograms include needles that are inserted through the skin, electrode-gel coupled sensors, and the like. A gas sensing display module 48 is provided to sense and display the amount of various gases in a patient's bloodstream, airway, or skin/cutaneous surface. For example, module 48 may be employed to sense the amount of oxygen saturation, $CO_2$ saturation, and the like. Optionally, module 48 may include a thermistor or thermocouple-based temperature measuring device that may be placed against or inserted into the skin to measure the patient's body temperature.

A drug delivery control module 50 may optionally be provided to supply various drugs to the patient. For example, module 50 may be a passive device for delivering nitroglycerine. Alternatively, module 50 may be an active device for electrophoretic delivery of drugs such as vasopressin, an anti-arrhythmic drug, and the like. In this way, module 50 provides device 10 with the ability to transcutaneously deliver drugs as device 10 is placed against the patient's body to perform CPR.

Although one embodiment illustrates the use of a compression member to sense when the chest is being compressed, it will be appreciated that other techniques may be provided to sense chest compression. For example, electrodes may be placed on the chest and sensors employed to detect electrical impulses or a change in impedance as the chest is compressed. Alternatively, a pressure sensor may be provided in an airway device to detect an increase in airflow in the patient's airway. The electrodes may be coupled to an external defibrillator-pacer that is capable of delivering low energies, i.e. about 0.01 amps to about 2 amps, and more preferably about 0.1 amps to about 1.0 amps, to stimulate the diaphragm or other respiratory muscles. In this way, a system is provided which may provide respiratory muscle stimulation (that is coordinated with chest compressions), pacing, and defibrillation.

Referring now to FIG. 7, an exemplary method for performing CPR using device 10 will be described. As shown, device 10 is placed on the patient such that compression member 12 is placed over the sternum and end elements 18 and 20 are placed over the ribs. As previously described, the particular location and arrangement of end elements 18 and 20 may be varied to optimize respiratory muscle stimulation. The rescuer then compresses compression member 12, preferably by placing both hands on compression member 12 and pushing downward. Compression of compression member 12 proceeds in a manner similar to that performed when performing traditional CPR. Immediately after the maximum compression is applied, electrodes on end elements 18 and 20 are actuated to stimulate the diaphragm and/or the chest wall muscles to contract during the relaxation or decompression phase. Conveniently, power is supplied to the electrodes via an external defibrillator 52, although other energy sources may be employed as previously described. The electrodes may be actuated during every relaxation or decompression phase or during only selected relaxation or decompression phases, depending on the need of the patient. Since device 10 is coupled to the defibrillator 52, the patient may also be supplied with a defibrillation shock or cardiac pacing. Hence, defibrillator 52 may be used to stimulate respiratory muscle contraction as well as to pace and/or defibrillate the heart. In that case, the sensor may be configured to be the same electrodes used to defibrillate the patient so that no compression member would be needed.

To stimulate respiratory muscles contract, the current supplied by the electrodes is preferably in the range from about 0.01 amps to about 2.5 amps, and more preferably from about 0.1 amps to about 1.0 amps. However, it will be appreciated that the specific amount of current will depend on chest wall impedance and mode of stimulation, e.g., square wave impulse, unipolar wave forms, biphasic wave forms, multiphasic wave forms, multi-vectorial pathways, use of pulse trains, and the like. In some cases it may be desirable to stimulate one side of the diaphragm or chest wall at a different time from the other side of the diaphragm or chest wall, e.g., by about 10 msec to about 50 msec, to reduce the risk of shock to the rescuer. The respiratory muscles are preferably stimulated to contract at a frequency in the range from about 30 to 120 times per minute.

Periodically, about every two to ten compressions, the patient is ventilated. Ventilation may be accomplished using an automated ventilator which may or may not be coupled to device 10. Alternatively, various manual ventilators may be employed as is known in the art. In one particular embodiment, a ventilation device is coupled with a threshold valve so that the duration and extent of negative intrathoracic pressure may be controlled during the relaxation or decompression phase as previously described. A pressure sensor and feedback loop circuit may also be used to measure the negative intrathoracic pressure in the airway and adjust the energy delivered to the electrode to maintain a generally constant negative intrathoracic pressure caused by each contraction of the respiratory muscles.

Figure 8:
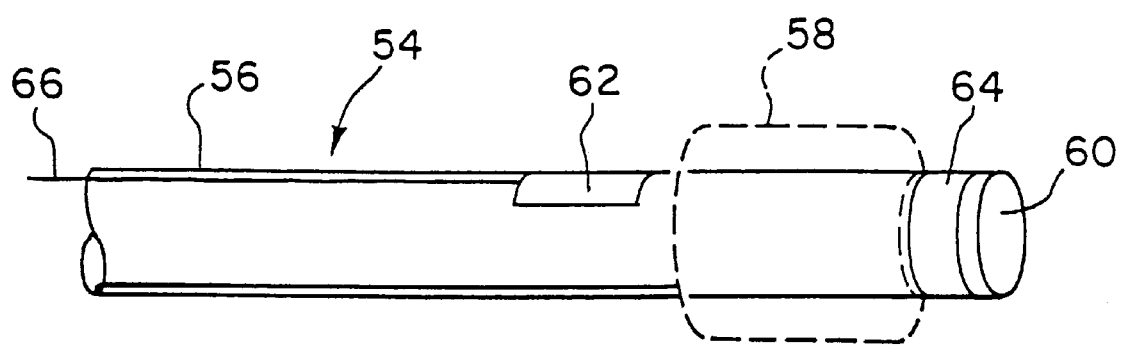
FIG. 8 illustrates an exemplary endotracheal tube having a pair of electrodes to electrically stimulate the phrenic nerve according to the invention.

Referring now to FIG. 8, an alternative embodiment of a device 54 for stimulating the respiratory muscles to contract will be described. Device 54 comprises an endotracheal tube 56 having an inflatable member 58 (shown in phantom line) which serves to secure endotracheal tube 56 in the patient's airway as is known in the art. Endotracheal tube 56 includes a lumen 60 through which the patient is ventilated. Device 54 further includes a pair of electrodes 62 and 64 which operate in a bipolar manner to electrically stimulate the phrenic nerve. In turn, stimulation of the phrenic nerve causes the diaphragm and chest wall muscles to contract. An electrical lead 66 is provided to supply electrical current to electrode 62.

In this way, when device 54 is inserted into the patient's airway, electrodes 62 and 64 are positioned so that when current is supplied to electrode 62, the phrenic nerve is electrically stimulated to cause the respiratory muscles to contract. As with other embodiments described herein, electrode 62 is preferably actuated during the relaxation or decompression phase of CPR so that the respiratory muscles contract to increase the magnitude and extent of negative intrathoracic pressure during the decompression phase. Optionally, lead 66 may be coupled to a controller of a compression device which is similar to compression member 12 so that electrical stimulation of the phrenic nerve may be coordinated with chest compression. In a similar manner, lead 66 may be coupled to a ventilator which supplies air through lumen 60 so that ventilation may also be coordinated in a manner similar to that described with previous embodiments.

In another alternative, endotracheal tube 54 may be provided with electrodes to pace the heart. Such electrodes may be configured in a bipolar or monopolar manner, and may optionally be connected with an external electrode or an esophageal electrode.

Although described in the context of an endotracheal tube, it will be appreciated that electrical stimulation of the phrenic nerve may be accomplished by placing electrodes on a laryngeal mask airway, or other ventilation device which is placed within the larynx, esophagus, or trachea. Further, one or more electrodes may be included on a laryngeal mask airway or endotracheal tube that is inserted into the esophagus to pace the heart and/or to stimulate the phrenic nerve. As one example, such an electrode may be placed on an airway as described in U.S. Pat. No. 5,392,774, the disclosure of which is herein incorporated by reference. As another alternative, an electrical stimulator may be placed externally over the neck to stimulate the phrenic nerve. In still a further alternative, a magnetic field may be produced about the phrenic nerve to stimulate the diaphragm or chest wall muscles to contract. Devices for producing such an electrical field may be placed within the airway or externally about the neck.

Figure 8A:
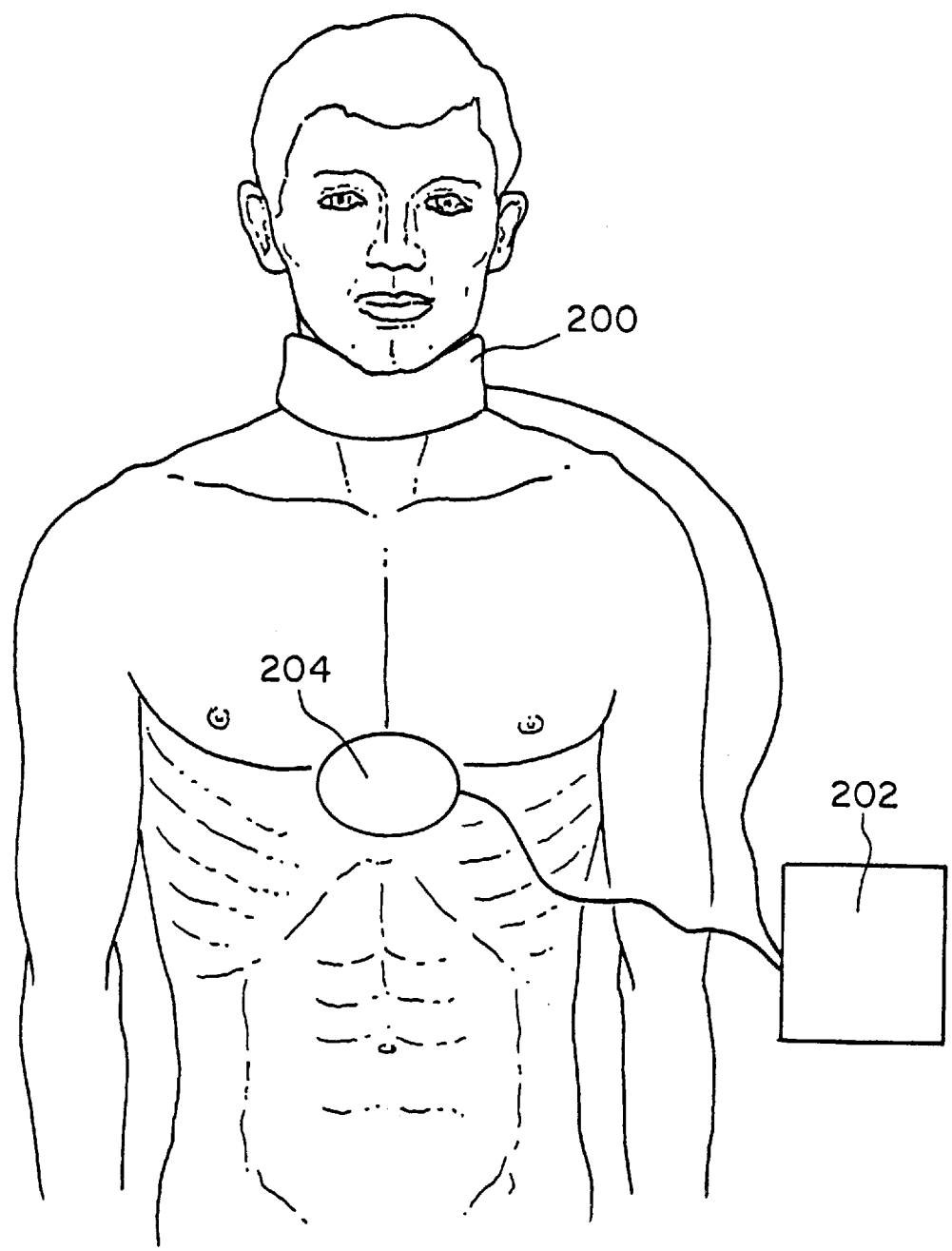
FIG. 8A illustrates a collar to electrically or magnetically stimulate diaphragmatic stimulation according to the invention.

One particular embodiment of a device 200 for either electrically or magnetically stimulating the phrenic nerve is illustrated in FIG. 8A. Device 200 comprises a collar having one or more electrodes or elements to produce electrical current or a magnetic field to stimulate the phrenic nerve. Device 200 is coupled to a controller 202 having a power source. Also coupled to controller 202 is a compression sensor 204 so that respiratory muscle stimulation may be coordinated with chest compressions as previously described.

In one particular embodiment, the invention may employ the use of a mechanical chest compressor which is coupled to a ventilator as described in U.S. Pat. No. 4,397,306, previously incorporated by reference. The stimulating electrodes may be coupled to the chest compressor or ventilator via a controller so that the controller may coordinate chest compression, ventilation, respiratory muscle stimulation, defibrillation, pacing, as well as other features previously described. Further, the amount of negative intrathoracic pressure generated with each contraction of the respiratory muscles may be used to adjust the energy needed for subsequent contractions. Such a system may conveniently be located in an emergency vehicle or a health care facility.

Figure 9:
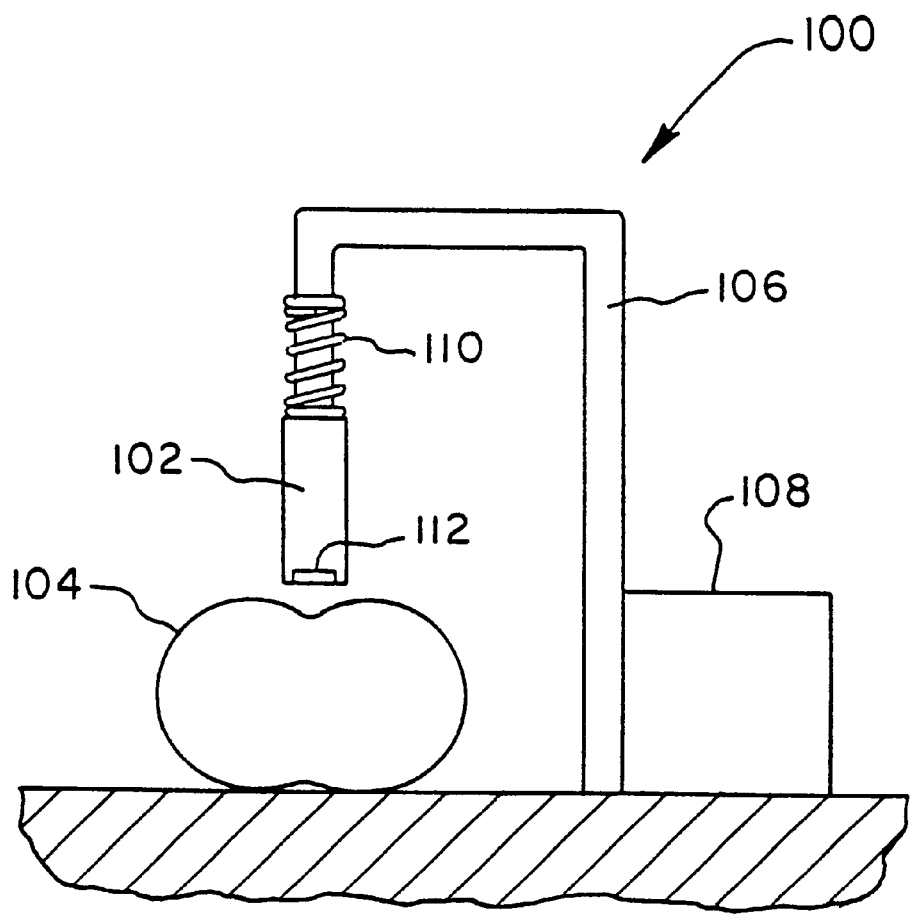
FIG. 9 is a schematic diagram of an exemplary system for stimulating the respiratory muscles to contract while performing CPR.

For example, one such system 100 is illustrated schematically in FIG. 9 and comprises a compression piston 102 that is held over a patient's thorax 104 by a support arm 106. Compression piston 102 is powered by an electric or pneumatic motor 108. When in use, piston 102 moves downward to compress the patient's chest. After the compression phase is complete, a spring 110, or other return mechanism, lifts piston 102 from the patient's chest to maximize the negative intrathoracic pressure during the relaxation phase. A controller is included with motor 108, and piston 102 includes a sensor 112 so that the respiratory muscles may be triggered to contract during the relaxation or decompression phase. The controller may optionally be coupled to a ventilator, a defibrillator, a heart pacer, a drug delivery system, various other sensors and/or an airway occluding device as previously described.

Figure 10:
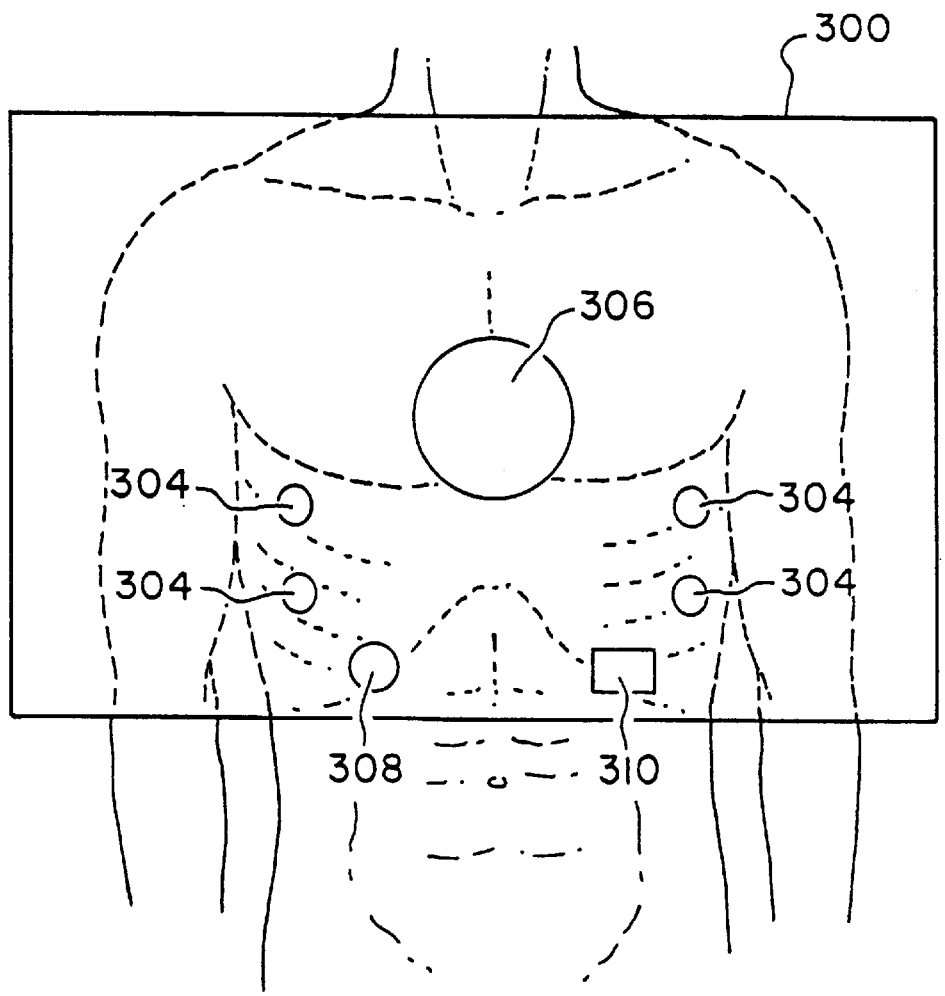
FIG. 10 illustrates a blanket having electrodes for stimulating the respiratory muscles to contract according to the invention.

Still another embodiment of a device 300 for stimulating the respiratory muscles to contract is illustrated in FIG. 10. Device 300 comprises an insulated blanket 302 which is constructed of an electrically insulative material, such as rubber, to protect the rescuer against possible shocks. Blanket 302 may incorporate any of the elements of other embodiments described herein to assist in respiratory muscle stimulation, monitoring, drug delivery, sensing, defibrillation, pacing, and the like. For example, blanket 302 includes electrodes 304 which may be selectively located to stimulate respiratory muscle stimulation. For example, electrodes 304 may be placed over the lower margin of the rib cage as previously described, or over the abdomen to stimulate the abdomen. A compression sensor 306 is provided to coordinate chest compressions with activation of electrodes 304. A potentiometer 308 is included to regulate the amount of current supplied by electrodes 304. A power supply 310 is further provided to supply current to electrodes 304.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A method for increasing cardiopulmonary circulation when performing cardio pulmonary resuscitation which involves a compression phase and a decompression phase, the method comprising:
   actively compressing a patient's chest during the compression phase; and
   stimulating at least some of the respiratory muscles to contract to cause an increase in the magnitude and duration of negative intrathoracic pressure during the decompression phase, thereby enhancing the amount of venous blood flow into the heart and lungs.

2. A method as in claim 1, wherein the respiratory muscles are stimulated to contract at a frequency in the range from about 30 to about 120 times per minute.

3. A method as in claim 1, wherein the stimulating step comprises delivering electrical current to the diaphragm.

4. A method as in claim 1, wherein the stimulating step comprises delivering electrical current to the phrenic nerve.

5. A method as in claim 1, further comprising stimulating the respiratory muscles to contract only during the decompression phase.

6. A method as in claim 1, further comprising periodically supplying respiratory gases to the patient's lungs to ventilate the patient.

7. A method as in claim 1, further comprising periodically occluding airflow to the lungs during at least a portion of the decompression phase by placing an impedance valve into the patient's airway, wherein the impedance valve comprises a valve housing and a valve member that is movable between an open position and a closed position, and wherein the valve member is set to move to the open position after experiencing a predetermined threshold negative intrathoracic pressure.

8. A method as in claim 1, further comprising sensing when the patient's chest is actively compressed and stimulating the respiratory muscles to contract after sensing the chest compression.

9. A method as in claim 1, wherein the stimulating step comprises delivering electrical current to the chest wall muscles.

10. A method as in claim 1, wherein the stimulating step comprises delivering magnetic energy to the phrenic nerve.

11. A device to assist in the performance of a cardio pulmonary resuscitation procedure, the device comprising:
   a compression member which is adapted to be placed in the proximity of the sternum and to be operated to compress the chest, the compression member including a sensor to determine when the patient's chest has been compressed; and
   at least one electrode coupled to the sensor that is adapted to deliver electrical current to at least some of the respiratory muscles to cause the stimulated respiratory muscles to contract, wherein the electrode is adapted to deliver the electrical current to the respiratory muscles based on information from the sensor regarding the state of chest compression.

12. A device as in claim 11, further comprising a pair of arms extending from the compression member, and wherein said at least one electrode is coupled to an end of one of the arms, and further comprising a second electrode that is coupled to an end of the other arm, with the arms separating the two electrodes.

13. A device as in claim 12, wherein the arms extend downward from the compression member so as to be adapted to be received over a lower portion of the rib cage when the compression member is over the sternum.

14. A device as in claim 12, further comprising an actuator coupled to the compression sensor, the actuator actuating the electrode with electric current when an appropriate number of compressions have been sensed.

15. A method for increasing cardiopulmonary circulation when performing cardio pulmonary resuscitation which involves a compression phase and a decompression phase, the method comprising:

actively compressing a patient's chest during the compression phase;

sensing compression of the patient's chest; and stimulating at least some of the respiratory muscles to contract after sensing the chest compression to cause an increase in the magnitude and duration of negative intrathoracic pressure during the decompression phase, thereby enhancing the amount of venous blood flow into the heart and lungs.

16. A method as in claim 15, wherein the respiratory muscles are stimulated to contract at a frequency in the range from about 30 to about 120 times per minute.

17. A method as in claim 15, wherein the stimulating step comprises delivering electrical current to the diaphragm.

18. A method as in claim 15, wherein the stimulating step comprises delivering electrical current to the phrenic nerve.

19. A method as in claim 15, wherein the stimulating step comprises delivering electrical current to the chest wall muscles.

20. A method as in claim 15, wherein the stimulating step comprises delivering magnetic energy to the phrenic nerve.

* * * * *